United States Patent [19]
Thompson et al.

[11] Patent Number: 5,900,400
[45] Date of Patent: *May 4, 1999

[54] SERINE PROTEASE INHIBITOR ANALOGS

[75] Inventors: Robert C. Thompson, Boulder, Colo.; Kjell Ohlsson, Glemminge Prastgard, Sweden

[73] Assignee: Amgen Inc., Thousand Oaks, Calif.

[*] Notice: This patent is subject to a terminal disclaimer.

[21] Appl. No.: 08/283,477

[22] Filed: Jul. 29, 1994

Related U.S. Application Data

[63] Continuation of application No. 07/807,769, Dec. 6, 1991, abandoned, which is a continuation of application No. 07/581,126, Sep. 10, 1990, abandoned, which is a continuation of application No. 07/205,372, Jun. 10, 1988, abandoned, which is a continuation-in-part of application No. 06/803,423, Dec. 2, 1985, Pat. No. 4,760,130, which is a continuation-in-part of application No. 06/678,823, Dec. 6, 1984, abandoned.

[51] Int. Cl.$^6$ .......................... A61K 38/55; C12N 15/15; C07K 14/81
[52] U.S. Cl. ................................ 514/2; 514/12; 530/300; 530/324; 530/854; 530/350; 435/69.2; 435/172.1; 435/213; 435/218
[58] Field of Search .................................. 435/69.2, 218, 435/213, 172.1; 530/324, 300, 350, 854; 514/2, 12

[56] References Cited

U.S. PATENT DOCUMENTS

| | | | |
|---|---|---|---|
| 4,394,443 | 7/1983 | Weissman et al. | 435/6 |
| 4,511,503 | 4/1985 | Olson et al. | 260/112 |
| 4,530,901 | 7/1985 | Weissman | 435/70 |
| 4,546,082 | 10/1985 | Kurgan et al. | 435/172.3 |
| 4,595,674 | 6/1986 | Tschesche | 514/9 |
| 4,626,510 | 12/1986 | Grandi | 435/317 |
| 4,652,639 | 3/1987 | Stabinsky | 536/27 |
| 4,672,032 | 6/1987 | Slavkin et al. | 435/68 |
| 4,711,848 | 12/1987 | Insley et al. | 435/91 |
| 4,720,454 | 1/1988 | White et al. | 435/6 |
| 4,760,130 | 7/1988 | Thompson et al. | 530/350 |
| 4,788,135 | 11/1988 | Davis et al. | 435/6 |
| 4,845,076 | 7/1989 | Heinzel | 530/324 |
| 4,923,807 | 5/1990 | Webb et al. | 435/69.2 |
| 4,952,512 | 8/1990 | Loskutoff et al. | 435/320 |
| 5,102,995 | 4/1992 | Tollefsen et al. | 536/27 |
| 5,109,113 | 4/1992 | Caras et al. | 530/350 |
| 5,151,438 | 9/1992 | Sham et al. | 514/357 |
| 5,157,019 | 10/1992 | Glover et al. | 514/12 |
| 5,196,404 | 3/1993 | Maraganore et al. | 514/13 |
| 5,215,915 | 6/1993 | Tiberi et al. | 435/252.3 |
| 5,252,725 | 10/1993 | Rubin et al. | 536/23.5 |
| 5,376,633 | 12/1994 | Lezdey et al. | 514/8 |
| 5,532,215 | 7/1996 | Lezdey et al. | 514/8 |

FOREIGN PATENT DOCUMENTS

| | | |
|---|---|---|
| 114 506 | 8/1984 | European Pat. Off. |
| 84 03 711 | 9/1984 | WIPO |
| 86 03 497 | 6/1986 | WIPO |
| 86 03 519 | 6/1986 | WIPO |

OTHER PUBLICATIONS

Ohlsson et al., *Chemical Abstracts*, (1983), No. 99:173443.
Eisenberg, S.P., et al., "Location of the Protease–inhibitory Region of Secretory Leukocyte Protease Inhibitor," *The Journal of Biological Chemistry*, 265:7976–7981 (1990).
Wong, Y. N., et al. (1994), "A pharmacokinteic evaluation of HIV protease inhibitors, cyclic ureas, in rats and dogs," *Biopharmaceutics & Drug Disposition*, 15:535–544.
Dorsey, B. D., et al. (1994), "Synthesis and evaluation of pyridyl analogs of L–735,524: Potent HIV–1 portease inhibitors," *Bioorganic & Medicinal Chemistry Letters*, 4:2769–2774.
Rose, J. R., et al. (1994), "Structure–assisted design of nonpeptide human immunodeficiency virus–1 protease inhibitors," *American Journal of Respiratory and Critical Care Medicine*, 150:S176–S182.
Chen, Z., et al. (1995), "Three–dimensional structure if a mutant HIV–1 protease displaying cross–resistance to all protease inhibitors in clinical trials," *The Journal of Biological Chemistry*, 270:21433–21436.
Maschera, B., et al. (1995), "Analysis of resistance to human immunodeficiency virus type —protease inhibitors by using matched bacterial expression and proviral infection vectors," *Journal of Virology*, 69:5431–5436.
Amann et al. (1983), "Vectors bearing a hybrid trp–lac promoter userful for regulated expression of cloned genes in *Escherichia coli*," *Gene*, 25:167–178.
Anderson et al. (1983), "Isolation of a genomic clone for bovine pancreatic trypsin inhibitor by using a unique–sequence synthetic DNA probe," *Proc. Natl. Acad. Sci. USA*, 80:6838–6842.
Botstein et al. (1982), "Principles and Practice of Recombinant DNA Research with Yeast," *The Molecular Biology of the Yeast Sacchromyces*, 607–636.
Brake et al. (1984), "α–Factor–directed synthesis and secretion of mature foreign proteins in *Saccharomyces cerevisiae*," *Proc. Natl. Acad. Sci. USA*, 81:4642–4646.
Fritz (1988), "Human Mucus Proteinase Inhibitor (Human MPI)," *Biol. Chem. Hoppe–Seyler*, 369:79–82.
Fritz et al. (1978), "Naturally Occurring Low Molecular Weight Inhibitors of Neutral Proteinases from PMN–Granulocytes and of Kallikreins," *Agents and Actions*, 8/1–2:57–64.
Kurachi et al. (1981), "Cloning and sequence of cDNA coding for $a_1$–antitrypsin," *Proc. Nat'l. Acad. Sci. USA*, 78:6826–6830.

(List continued on next page.)

*Primary Examiner*—Sally Teng
*Attorney, Agent, or Firm*—Finnegan, Henderson, Farabow, Garrett & Dunner, L.L.P.

[57] ABSTRACT

Analogs of the serine protease inhibitors in which the amino acid sequence is varied slightly are disclosed, which analogs variously show improved properties including improved resistance to oxidative inactivation, improved ability to inhibit pancreatic elastase, improved ability to inhibit cathepsin G, and improved ability to inhibit trypsin.

37 Claims, No Drawings

OTHER PUBLICATIONS

Landau et al. (1984), "Cloning of a terminal transferaase cDNA by antibody screening," Proceedings, *National Academy of Sciences USA*, 81:5836–5840.

Leicht et al. (1982), "Sequence homology and structural comparison between the chromosomal human $a_1$–antitrypsin and chicken ovalbumin genes," *Nature*, 297:655–659.

Leytus et al. (1984), "Characterization of cDNA coding for human factor X," *Proceedings, National Academy of Sciences USA*, 81:3699–3702.

Lovett et al. (1979), "*Bacillus subtilis* as a Host for Molecular Cloning," *Methods in Enzymology*, 68:342–357.

Maniatis (1982), *Molecular Cloning, A Laboratory Manual*, Cold Spring Harbor Laboratory Press, p. 231.

Maniatis (1982), *Molecular Cloning, A Laboratory Manual*, Cold spring Harbon Laboratory Press, pp. 190–193.

Miller et al. (1981), "Synthesis of Biologically Active Proteins by Recombinant DNA Technology," *Drug Development Research*, 1:435–454.

Ohlsson et al. (1977), "Isolation and Partial Charcterization of a Low Molecular Weight Acid Stable Protease Inhibitor from Human Bronchial Secretion," *Hoppe–Seyler's Z. Physiol. Chem.*, 358:583–589.

Ohlsson et al. (1983), "Quantification of Granulocyte Elastase Inhibitors in Human Mixed Saliva and in Pure Parotid Secretion," *Hoppe–Seyler's Z. Physiol. Chem.*, 364:1323–1328.

Ohlsson et al. (1984), "Localization of antileukoprotease in the parotid and the submandibular salivary glands," *Biological Abstracts*, 78:ref. No. 90008 and Acta Otolaryngol (Stockh) (1984), 98:147–151.

Alberts et al. (1983), "Recombinant DNA Technology," *Molecular Biology of the Cell*, Garland Publishing Inc., pp. 185–196.

Rogers et al. (1983), "The Isolation of a Clone for Human a 1–Antitrypsin and the Detection of a 1–Antitrypsin in mRNA From Liver and Leukocytes," *Biochem and Biophysical Res. Commun.*, 116(2):375–382.

Schiessler et al. (1976), "Inhibitors of Acrosin and Granulocyt–Proteinase from Human Genital Tract Secretions," *Hoppe–Seyler's Z. Physiol. Chem. Bd.*, 357:1251–1260.

Schiessler et al., "Acid–stable inhibitors of granulocyte neutral proteases in human mucous secretions: biochemistry and possible biological function," *Chemical Abstracts*, 89:192866u (1978) and *Neutral Proteases of Human Polymorphonuclear Leukocytes*, Urban & Schwarzenberg, Baltimore/Munich, pp. 195–207 (1978).

Schiessler et al. (1979), "Inhibitors of granulocyte protease (antileukoprotease) in human genital tract secretions," *Chemical Abstracts*, 90: abstract No. 117084e and Human Fertilization, Georg Thieme Publishers, Stuttgart (1978), pp. 101–106.

Seemuller et al. (1986), "The acid–stable proteinase inhibitor of human mucous secretions (HUSI–I, antileukoprotease)," *FEBS Lett.*, 199:43–48.

Stetler et al. (1986), "Isolation and sequence of a human gene encoding a potent inhibitor of leukocyte proteases," *Nucleic Acids Research*, 14(20) :7883–7896.

Travis et al. (1983), "Human Plasma Proteinase Inhibitors," *Ann. Rev. Biochem.*, 52:655–709.

Valenzuela et al. (1982), "Synthesis and assembly of hepatitis B virus surface antigen particles in yeast," *Nature*, 298:347–350.

Young et al. (1983), "Efficient isolation of genes by using antibody probes," *Proc. Natl. Acad. Sci. USA*, 80:1194–1198.

Wallner et al. (1974), "Characterization of an Acid–Stable Proteinase Inhibitor in Human Cervical Mucus," *Hoppe–Seyler's Z. Physiol. Chem. Bd.*, 355:709–715.

Stetler et al. (1989), "Secretion of Active, Full–and Half–[ ] Human Secretory Leukocyte Protease Inhibitor by *Saccharomyces Cerevisiae*," *Bio/Technology*, 7(1):55–60.

Smith et al. (1985), "Human bronchial leucocyte proteinase inhibitor," *Biochem. Journal*, 225:463–472.

Lucey et al. (1990), "Recombinant human secretory leukocyte–protease inhibitor; In vitro properties, and amelioration of human neutrophil elastase–induced emphysema and secretory cell metaplasia in the hamster,"*J. Lob. Clin. Med.*, 115/2:224–232.

Birrer et al. (1992), "Intravenous recombinant secretory leukoprotease inhibitor augments antineutrophil elastase defense," *Journal of Applied Physiology*, 73/1:317–323.

Klasen, et al. (1985), "The N–Terminal Sequence of Antileukoprotease Isolated from Bronchial Secretion," *Chemical and Biophysical Research Communications*, 128/1:285–289.

Movva, et al. (1980), "Gene Structure of the OmpA Protein, a Major Surface Protein of *Escherichia coli* Required for Cell–Cell Interaction," *J. Mol. Biol.*, 143:317–328.

Whitson, et al. (1986), "Thermodynamic Analysis of the Lactose Repressor—Operator DNA Interaction," *Biochemistry*, 25:3852–3858.

Whitson, et al. (1986), "Dissociation of the Lactose Repressor—Operator DNA Complex: Effects of Size and Sequence Context of Operator–Containing DNA," *Biochemistry*, 25:3845–3852.

Chang, et al. (1986), "*Saccharomyces cerevisiae* Secretes and Correctly Processes Human Interferon Hybrid Proteins Containing Yeast Invertase Signal Peptides," *Molecular and Cellular Biology*, 6:1812–1819.

Julius et al. (1984), "Isolation of the Putative Structural Gene for the Lysine–Arginine–Cleaving Endopeptidase Required for Processing of Yeast Prepro–α–Factor," *Cell*, 37:1075–1089.

Broach, James R. (1983), "Construction of High Copy Yeast Vectors Using 2μm Circle Sequences," *Methods In Enzymology*, 101:307–325.

Emr et al. (1983), "An MFα1–SUC2 (α–factor–invertase) gene fusion for study of protein localization and gene expression in yeast," *Proc. Natl. Acad. Sci. USA*, 80:7080–7084.

Derynck et al. (1984), "Human Transforming Growth Factor–α: Precursor Structure and Expression in *E. coli*," *Cell*, 38:287–297.

Van Arsdell et al. (1987), "The Yeast Repeated Element Sigma Contains a Hormone–Inducible Promoter," *Molecular and Cellular Biology*, 7/2:749–759.

Kurjan et al. (1982), "Structure of a Yeast Pheromone Gene (MFα) : A Putative α–Factor Precursor Contains Four Tandem Copies of Mature α–Factor," *Cell*, 30:933–943.

Swift et al. (1982), "Rat pancreatic kallikrein mRNA: Nucleotide sequence and amino acid sequence of the encoded preproenzyme," *Proc. Natl. Acad.Sci. USA*, 79:7263–7267.

*Chemical Abstracts*, vol. 100, (1984), No. 46033z.

*Chemical Abstracts*, vol. 97, (1982), No. 51668j.

*Chemical Abstracts*, vol. 95, (1981), No. 2484w.

*Chemical Abstracts*, vol. 95, (1981), No. 169751.

*Chemical Abstracts,* vol. 84, (1975), No. 28236.

Thompson et al. (1986), "Isolation, properties, and complete amino acid sequence of human secretory leukocyte protease inhibitor, a potent inhibitor of leukocyte elastase," *Proc. Natl. Acad. Sci. USA,* 6692–6696.

Kramps et al. (1990), "Proteinase inhibitor activities of antileukoprotease are represented by its second COOH–terminal domain," *Biochimica et Biophysica Acta,* 1038/2:178–185.

Böhm et al. (1991), "Purification of a serine–proteinase inhibitor from human articular cartilage," *Biochem. J.,* 274:269–273.

Hirsch, M. S. (1988), "Antiviral Drug Development for the Treatment of Human Immunodeficiency Virus Infections," *The American Journal of Medicine,* 85:182–185.

Creighton, T. E. (1983), "Proteins: Structures and Molecular Principles," Freeman & Company, NY, pp.93–94.

Rice et al. (1990), "Regulation of Proteolysis at the Neutrophil–Substrate Interface by Secretory Leukoprotease Inhibitor," *Science,* 249:178–181.

Schiessler et al. (1977), The Uterine Cervix in Reproduction, "The Acid–stable Proteinase Inhibitor (Antileukoprotease) of Human Cervical Mucus," Georg Thieme Publishers Stuttgart, pp. 84–89.

Wengenmayer (1983), "Synthesis of Peptide Hormones Using Recombinant DNA Techniques," *Angew. Chem. Int. Ed. Engl.,* 22:842–858.

Anon (1994), "Aids drugs: Beyond access," *The Economist of January 8th 1994,* p. 79.

Fritz (1980), "Proteinase inhibitors in severe inflammatory processes (septic shock and experimental endotoxaemia) : biochemical, pathophysiological and therapeutic aspects," *Protein Degradation in Health and Disease, Ciba Foundation Symposium,* 75:351–379.

Ghrayeb et al. (1984), "Secretion cloning vectors in *Escherichia coli,*" *The EMBO J.,* 3:2437–2442.

Helfman et al. (1983), "Identification of clones that encode chicken tropomyosin by direct immunological screening of a cDNA expression library," *Proceedings, National Academy of Sciences USA,* 80:31–35.

Hewick et al. (1981), "A Gas–Liquid solid Phase Peptide and Protein sequenator," *J. of Biological Chemistry,* 256(15):7990–7997.

Kueppers (1971), "Proteinase Inhibitor in Human Tears," *Biochem. Biophys. Acta.* 229:845–849.

Ohlsson et al., Pulmonary Emphysema and Proteolysis, pp. 307–324, 1987, Academic Press.

Darnell et al., Molecular Cell Biology, pp. 54–55 and 258–260, 1986, Scientific American Books, Inc.

Creighton, T.E. in "Proteins: Structure and Molecular Principles", Freeman & Company, NY 1983.

SERINE PROTEASE INHIBITOR ANALOGS

This application is a continuation of application Ser. No. 07/807,769, filed Dec. 6, 1991, now abandoned, which is a continuation of application Ser. No. 07/581,126, filed on Sep. 10, 1990, now abandoned, which is a continuation of Ser. No. 07/205,372 filed on Jun. 10, 1988, abandoned, which is a continuation-in-part of Ser. No. 06/803,423 filed on Dec. 2, 1985 which issued to U.S. Pat. No. 4,760,130 on Jul. 26, 1988, which is a continuation-in-part of Ser. No. 06/678,823 filed Dec. 6, 1984, abandoned.

BACKGROUND OF THE INVENTION

Endogenous proteolytic enzymes serve to degrade invading organisms, antigen-antibody complexes and certain tissue proteins which are no longer necessary or useful to the organism. In a normally functioning organism, proteolytic enzymes are produced in a limited quantity and are regulated in part through the synthesis of protease inhibitors.

A large number of naturally occurring protease inhibitors serve to control the endogenous proteases by limiting their reactions locally and temporally. In addition, the protease inhibitors may inhibit proteases introduced into the body by infective agents. Tissues that are particularly prone to proteolytic attack and infection, e.g. those of the respiratory tract, are rich in protease inhibitors.

Protease inhibitors comprise approximately 10% of the human plasma proteins. At least eight inhibitors have been isolated from this source and characterized in the literature. These include $\alpha_2$-macroglobulin ($\alpha_2$M), $\alpha_1$-protease inhibitor ($\alpha_1$PI), $\alpha_1$-antichymotrypsin ($\alpha_1$Achy), $\alpha_1$-anticollagenase ($\alpha_1$AC), and inter-$\alpha$-trypsin inhibitor (I$\alpha$I).

A disturbance of the protease/protease inhibitor balance can lead to protease-mediated tissue destruction, including emphysema, arthritis, glomerulonephritis, periodontitis, muscular dystrophy, tumor invasion and various other pathological conditions. In certain situations, e.g. severe pathological processes such as sepsis or acute leukemia, the amount of free proteolytic enzymes present increases due to the release of enzyme from the secretory cells. In addition, or separately in other situations, a diminished regulating inhibitor capacity of the organism may also cause alterations in the protease/protease inhibitor balance. An example of such a diminished regulating inhibitor capacity is an $\alpha_1$-protease inhibitor deficiency, which is highly correlated with the development of pulmonary emphysema.

In organisms where such aberrant conditions are present, serious damage to the organism can occur unless measures can be taken to control the proteolytic enzymes. Therefore, protease inhibitors have been sought which are capable of being administered to an organism to control the proteolytic enzymes.

One protease that is of particular pharmacological interest is leukocyte elastase. Leukocyte elastase, when released extracellularly, degrades connective tissue and other valuable proteins. While it is necessary for a normally functioning organism to degrade a certain amount of connective tissue and other proteins, the presence of an excessive amount of leukocyte elastase has been associated with various pathological states, such as emphysema and rheumatoid arthritis. To counteract the effects of leukocyte elastase when it is present in amounts greater than normal, a protease inhibitor has been sought which is specific for leukocyte elastase. Such a protease inhibitor would be especially useful if it were capable of being isolated or prepared in a purified form and in sufficient quantities to be pharmaceutically useful In the past, at least two leukocyte elastase inhibitors have been identified in the literature. One protein, described in Schiessler et al., "Acid-Stable Inhibitors of Granulocyte Neutral Proteases in Human Mucous Secretions: Biochemistry and Possible Biological Function", in Neutral Proteases of Human Polymorphoneuclear Leucocytes, Havemann et al. (eds), Urban and Schwarzenberg, Inc. (1978), was isolated from human seminal plasma and sputum and was characterized as being approximately 11 Kda in size with tyrosine as the N-terminal amino acid. The literature reports of this protein have only furnished a partial amino acid sequence, but even this partial sequence indicates that this protein varies substantially from the proteins of the present invention. The reports of the sequence of this protein, in combination with the complete amino acid sequence data for proteins of the present invention, indicate to the present inventors that the product sequenced by Schiessler et al. may have been a degraded protein which was not a single-polypeptide chain.

A second protein, isolated in one instance from human plasma, has been named $\alpha_1$-protease inhibitor. Work on this protein has been summarized in a review by Travis and Salvesen, Annual Review of Biochemistry 52: 655–709 (1983). The reports of the amino acid sequence of this protein indicate that it too differs substantially from the proteins of the present invention.

Because of the substantial differences in structure between single-polypeptide-chain proteins of the present invention and any single-polypeptide-chain serine protease inhibitors of the prior art, the single-polypeptide-chain serine protease inhibitors of the prior art are not "substantially homologous" to the proteins of the present invention.

Trypsin is another protease of particular interest from a pharmacological standpoint. Trypsin is known to initiate degradation of certain soft organ tissue, such as pancreatic tissue, during a variety of acute conditions, such as pancreatitis. A variety of efforts have been directed toward the treatment of these conditions, without marked success, through the use of proteins which it was hoped would inhibit the action of trypsin. Illustrative of such efforts are attempts to use exogenous bovine trypsin inhibitors in treatment of human pancreatitis. While such techniques have been attempted in Europe, they have not been approved as effective by the U.S. Food and Drug Administration.

Thus, there is a need for a protease inhibitor effective in neutralizing excess trypsin in a variety of acute and chronic conditions. As was the case with the leukocyte elastase inhibitor discussed above, a trypsin inhibitor would be particularly useful if it could be isolated and prepared in a purified form and in sufficient quantities to be pharmaceutically useful.

Cathepsin G is another protease present in large quantities in leukocytes. Cathepsin G is known to be capable of degrading in vitro a variety of valuable proteins, including those of the complement pathway Pancreatic elastase is another protease which may have a role in pancreatitis. Thus, inhibitors for these proteases are also of potential pharmaceutical value.

Leukocyte elastase, trypsin, cathepsin G and pancreatic elastase are examples of a class of proteases known as serine proteases, which have elements of common structure and mechanism Their activity against different substrates and their sensitivity to different inhibitors are believed to result from changes in only a few amino acid residues By analogy, it is possible to conceive of a class of serine protease inhibitors, also having common elements of structure and mechanism, in which changes in a relatively few amino acids will result in inhibition of different proteases, and that at least one member of this class will inhibit every serine protease of the former class. The class of serine protease inhibitors would then be of substantial values Surprisingly, the present inventors have found a 12 Kda protease inhibitor, isolated in purified form from parotid secretions, in which the amino acid sequence varies greatly from the reported sequences of single-polypeptide-chain serine protease inhibitors. The protease inhibitor of the present invention is believed to have at least two active sites. One site exhibits leukocyte elastase inhibiting properties while a second site exhibits activity against trypsin. The present inventors have accurately sequenced the entire length of the novel protease inhibitor. This sequence is set forth more fully hereinafter

SUMMARY OF THE INVENTION

This invention relates to protease inhibitors generally and, more specifically, to inhibitors directed to human polymorphonuclear (PMN)-granulocyte proteases. In particular, this invention relates to inhibitors for serine proteases, including human leukocyte elastase and trypsin. Additionally, the present invention relates to biologically active analogs of these inhibitors.

An object of the present invention is to provide purified forms of protease inhibitors which are active against one or a combination of a variety of serine proteases.

An additional object of the present invention is the determination of the amino acid sequence of such protease inhibitors. A further object of the present invention includes providing purified forms of protease inhibitors which would be valuable as pharmaceutical preparations exhibiting activity against leukocyte elastase and other serine proteases. Furthermore, the identification of biologically active analogs of such protease inhibitors with enhanced or equivalent properties is also one of the objects of the invention.

Additional objects and advantages of the invention will be set forth in part in the description which follows, and in part will be obvious from the description or may be learned from practice of the invention. The objects and advantages may be realized and attained by means of the instrumentalities and combinations particularly pointed out in the appended claims.

To achieve the objects and in accordance with the purposes of the present invention, a protease inhibitor is disclosed which exhibits inhibitory activity against serine proteases, particularly elastases such as leukocyte elastase. The preferred inhibitors have been isolated in a purified form from parotid secretions. The protease inhibitors have the ability, after being fully denatured, to form or reform disulfide bonds and undergo appropriate non-covalent interactions necessary to assume or re-assume an active tertiary structure capable of expression of the desired serine protease inhibitor activity in the absence of any biochemical stimulus.

Preferred inhibitors of the present invention are purified, single-polypeptide-chain proteins having at least one active site exhibiting serine protease inhibitor activity and are substantially homologous to the native serine protease inhibitor isolated from parotid secretions. Preferrably, the serine protease inhibitor activity exhibited at the active site is biologically equivalent to that of the native inhibitor isolated from parotid secretions. Thus, particularly preferred inhibitors according to the present invention have the amino acid sequence:

$R_1$-Gly-Lys-Ser-Phe-Lys-Ala-Gly-Val-Cys-Pro-Pro-Lys-Lys-Ser-Ala-Gln-Cys-Leu-$R_2$-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-Tyr-Gly-Gln-Cys-$R_8$-$R_3$-$R_9$-Asn-Pro-Pro-Asn-Phe-Cys-Glu-$R_4$-Asp-Gly-Gln-Cys-Lys-Arg-Asp-Leu-Lys-Cys-Cys-$R_5$-Gly-$R_6$-Cys-Gly-Lys-Ser-Cys-Val-Ser-Pro-Val-Lys-$R_7$, wherein, $R_1$ and $R_7$ are the same or different and are selected from the group consisting of a substituted or unsubstituted amino acid residues or derivatives thereof; and $R_2$, $R_3$, $R_4$, $R_5$, $R_6$, $R_8$ and $R_9$ are the same or different and are selected from the group consisting of methionine, valine, alanine, phenylalanine, tyrosine, tryptophan, lysine, glycine and arginine.

The amino acids represented by the foregoing abbreviations are set forth in the description of the preferred embodiment.

Furthermore, other biologically active, improved analogs of the protease inhibitors of the present invention may be obtained by replacing various other amino acids in the inhibitor amino acid sequence.

Additionally, to achieve the objects and in accordance with the purposes of the present invention, pharmaceutical compositions containing, as at least one of the active ingredients, a protease inhibitor in accordance with the present invention or its biologically active analogs as set forth herein are disclosed.

DESCRIPTION OF THE PREFERRED EMBODIMENT

Reference will now be made in detail to the presently preferred embodiments of the invention, which, together with the following examples, serve to explain the principles of the invention.

As noted above, the present invention relates to protease inhibitors which have been isolated in a purified form Preferably, the serine protease inhibitors of the present invention are single-polypeptide-chain proteins which are substantially homologous to, and most preferably biologically equivalent to, native serine protease inhibitors isolated from human parotid secretions. By "biologically equivalent," as used throughout the specification and claims, it is meant that the compositions of the present invention are capable of preventing protease induced tissue damage of the same type, but not necessarily to the same degree, as the native protease inhibitors By "substantially homologous," as used throughout the ensuing specification and claims, is meant a degree of homology to the native parotid inhibitor in excess of that displayed by previously reported single-polypeptide-chain serine protease inhibitor proteins. Preferably, the degree of homology is in excess of 40%, most preferably in excess of 50%, with a particularly preferred group of proteins being in excess of 60% homologous with the native parotid inhibitor. The percentage homology as above described is calculated as the percentage of the components found in the smaller of the two sequences that may also be found in the larger of the two sequences, a component being understood as a sequence of four, contiguous amino acids.

The protease inhibitors of the present invention are remarkably resistant to denaturation by heat and acids and resistant to loss of activity when exposed to many proteolytic enzymes including chymotrypsin, mouse submaxillary protease and clostripain. These inhibitors also have the ability to form the necessary disulfide bonds and undergo appropriate non-covalent interactions to assume an active tertiary structure capable of expressing serine protease inhibitor activity in the absence of a biochemical stimulus or, if the disulfide bonds have broken and the non-covalent interactions have been disrupted, to re-form such bonds and interactions to regain such active tertiary structure in the absence of biochemical stimulus.

The preferred protease inhibitors of the present invention have been discovered in parotid secretions and, for the first time, have been isolated in a purified form. For the purposes of the present application, "pure form" or "purified form," when used to refer to the protease inhibitors disclosed herein, shall mean substantially free of other proteins which are not serine protease inhibitor proteins. Preferably, the protease inhibitors of the present invention are at least 90% pure and preferably 95% pure.

In a preferred form of the present invention, parotid secretions are obtained from humans. However, it is contemplated that parotid secretions obtained from other mammalian sources would be useful in producing protease inhibitors of equivalent activity to those of the present invention.

The protease inhibitors of the present invention may be isolated in pure form from parotid secretions by the method comprising:

(a) collecting mammalian parotid secretions;

(b) isolating the inhibitor from the parotid secretions by fractionating the proteinaceous material in the secretions;

(c) identifying the fractions which possess serine protease inhibitor activity, preferably leukocyte elastase inhibitor activity; and (d) concentrating the fractions exhibiting the serine protease inhibitor activity.

In this method, the mammalian parotid secretions may be collected by any known means. It is preferred that they be collected through the use of a suction apparatus fitted over the parotid gland duct to prevent introduction into the collected sample of other oral fluids which may contain enzymes which would substantially modify the inhibitor.

In a preferred embodiment, the proteinaceous material present in the parotid secretions is fractionated by separation of the material according to its ability to be bound to cation exchange materials in the presence of varying concentrations of saline solutions. It has generally been noted that the protease inhibitor of the present invention will be eluted from a strong cation exchange material present in chromatography column by a fraction of sodium chloride eluant ranging in concentration from 0.005 M to 1.0 M and more specifically in a concentration ranging from 0.4 M to 0.8 M. Other saline solution concentrations may be required, however, to elute the protease inhibitor depending on the properties of the particular cation exchange column.

The fractions thus obtained are screened for presence of serine protease inhibitor, preferably leukocyte elastase inhibitor, activity. Preferably, this is accomplished by mixing the fractions with a known concentration of protease, preferably leukocyte elastase, and assaying the residual active enzyme by virtue of its ability to hydrolyze methoxysuccinyl Ala-Ala-Pro-Val p-nitroanilide, as observed in a spectrophotometer. The proteinaceous materials of the identified fractions are then separated according to size, preferably by gel filtration. If a gel filtration separation is used, a preferred eluant is a 0.5 M sodium chloride solution. Fractions exhibiting such activity are then concentrated by means such as ultrafiltration to obtain a purified and concentrated form of the protease inhibitor.

Protease inhibitors isolated by the above method generally exhibit stoichiometric activity in relation to the serine protease, such as leukocyte elastase. By stoichiometric activity, it is meant that each molecule of protease inhibitor will react with and thereby significantly decrease the activity of one molecule of leukocyte elastase. In a solution of the preferred inhibitor of the present invention in which the inhibitor and leukocyte elastase are present in a concentration greater than or equal to $10^{-8}$ M, such inhibitor would react with at least 90% of an equivalent molecular amount of leukocyte elastase.

As noted above, the present inventors have succeeded in isolating a serine protease inhibitor from parotid secretions in a hitherto unavailable, purified form. Isolation of this enzyme in a purified form was a prerequisite step to the correct sequencing of the inhibitor and to the development of pharmaceutical compositions containing the protease inhibitor and its analogs.

A preferred protease inhibitor of the present invention has the amino acid sequence:

Ser-Gly-Lys-Ser-Phe-Lys-Ala-Gly-Val-Cys-Pro-Pro-Lys-Lys-Ser-Ala-Gln-Cys-Leu-Arg-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-Tyr-Gly-Gln-Cys-Leu-Met-Leu-Asn-Pro-Pro-Asn-Phe-Cys-Glu-Met-Asp-Gly-Gln-Cys-Lys-Arg-Asp-Leu-Lys-Cys-Cys-Met-Gly-Met-Cys-Gly-Lys-Ser-Cys-Val-Ser-Pro-Val-Lys-Ala.

The foregoing abbrevations correspond to the amino acid residues in the polypeptide as follows:

| Amino acid | Abbreviation |
| --- | --- |
| Alanine | Ala |
| Valine | Val |
| Leucine | Leu |
| Isoleucine | Ile |
| Proline | Pro |
| Phenylalanine | Phe |
| Tryptophan | Trp |
| Methionine | Met |
| Glycine | Gly |
| Serine | Ser |
| Threonine | Thr |
| Cysteine | Cys |
| Tyrosine | Tyr |
| Asparagine | Asn |
| Glutamine | Gln |
| Aspartic acid | Asp |
| Glutamic acid | Glu |
| Lysine | Lys |
| Arginine | Arg |
| Histidine | His |

It has been found that these protease inhibitors have more than one distinct domain. By more than one distinct domain it is meant that the protein has multiple active sites which are functional against different enzymes. The presence and location of these sites have been determined by the discovery of a substantial homology between at least two portions of the protease inhibitor. It is believed that the presence of distinct domains confers on the instant protease inhibitors the ability to inhibit a variety of serine proteases, including both leukocyte elastase and trypsin.

It has been further noted that, due to the plurality of distinct domains of these protease inhibitors, the protease inhibitors may serve as frameworks on which various other active sites may be constructed to create protease inhibitors having additional properties. The preferred embodiment of the present invention is a protease inhibitor that inhibits any serine protease including but not limited to leukocyte elastase, complement components $C_1$, $C_3$ and $C_5$, plasma kallikrein, cathepsin G and trypsin. These enzymes are all members of a class of proteases known as serine proteases that share a common mechanism and many structural features. It is believed that, through manipulation of a few amino acid side-chains on the protease inhibitors of the present invention, a multiplicity of inhibitors may be created, each being capable of inhibiting at least one member of the whole class of serine proteases. Furthermore, such side-chain modifications can be expected to yield a plurality of inhibitors having improved inhibitory properties with respect to particular members of the class of serine proteins described above.

The amino-acid-side-chain changes required to attain these goals are suggested by certain elements of structural similarity between the preferred inhibitor of the present invention and other serine protease inhibitors for which the important functional part of the inhibitor has been elucidated through X-ray crystallography. Those elements of structural similarity include amino acids 17 to 29 and amino acids 70 to 83 of the preferred serine protease inhibitor of the present invention described above. The changes suggested to improve the inhibitor's activity, either in terms of quantity or quality, toward trypsin-like serine proteases include changing one or more of amino acid 20 from Arg to Lys, amino acid 72 or 74 from Leu to Lys or Arg, and amino acid 73 from Met to Lys or Arg.

It has been demonstrated that residues P5, P4, P3, P2, P1, P1', and P2' of peptides (nomenclature of Schecter and Berger, Biochem, Biophys. Res. Commun., 27 157–162, 1967, incorporated herein by reference) can affect their interactions with leucocyte elastase (Nakajima et al., J. Biol. Chem 254 4027–4032, 1979, incorporated herein by reference) and other serine proteases. Residue Leu72 of SLPI has now been identified by site directed mutagenesis as residue P1 with respect to leucocyte elastase, chymotrypsin and trypsin. It follows that residue 71 of SLPI is residue P2 with respect to these enzymes, residue 69 is residue P4, residue 68 is residue P5, residue 73 is residue P1' and residue 74 is residue P2'. Changes of the amino acids at each of these positions can therefore be anticipated to affect the interactions of SLPI with these and other serine proteases. All substitutions at these positions to create novel inhibitors of serine proteases are, therefore, contemplated herein.

The present inventors have found that changing amino acid 72 from Leu to Arg confers upon the molecule the ability to inhibit plasma kallikrein. When Arg 72-SLPI is reacted with kallikrein, the resultant dissociation constant is $1.5 \times 10^{-6}$ M.

The three-dimensional structure of the SLPI molecule complexed to alpha chymotrypsin shows that two other regions of the molecule can contact a proteolytic enzyme bound, primarily, to Leu72. These include amino acids 89 and 90, of the secondary loop of domain 2, and amino acid 30 of domain 1. Preferred amino acid residues for substitutions include leucine, lysine, glutamic acid, and glutamine.

The changes suggested to improve the inhibitor's activity, either in terms of quantity or quality, toward chymotrypsin-like serine proteases, including cathepsin G, include changing one or more of amino acid 20 from Arg to Phe, Tyr or Trp, amino acid 72 or 74 from Leu to Phe Tyr, or Trp, and amino acid 73 from Met to Phe, Tyr, or Trp. In addition, amino acid 72, the elastase chymotrypsin active site, changed to any other amino acid.

The changes suggested to improve the inhibitor's activity either in terms of quantity or quality, toward pancreatic-elastase-like serine proteases include changing one or more of amino acid 20 from Arg to Ala amino acid 72 or 74 from Leu to Ala, and amino acid 73 from Met to Ala.

It must be borne in mind in the practice of the present invention that the alteration of amino acid sequences to confer new protease inhibiting properties on the present proteins may disrupt the inhibitor's activity toward leukocyte elastase or toward trypsin. Such effects may be determined by routine experimentation following the teachings of the present invention.

Further, it is contemplated that substitution of discrete amino acids or of discrete sequences of amino acids, as set forth above, may enhance either the leukocyte elastase inhibitory properties or the trypsin inhibitory properties of the present protease inhibitors while sacrificing some activity of the unenhanced domain. Indeed, the activity of any domain within the inhibitor protein may be deactivated entirely by appropriate amino acid substitutions, thereby creating inhibitor proteins which are specific for one or some subset of the enzymes against which the protein is normally active. For example, substitution of Gly for Arg in position 20 deactivates the trypsin inhibitory domain while substitution of Gly for Met in the 73 position or for Leu in the 72 or 74 position deactivates the leukocyte inhibitory domain. The domains may also be separated into separate proteins, each of which retains a desired inhibitory function. The present claims extend to other inhibitors produced by these means.

While the above-recited amino acid sequence yields a leukocyte elastase inhibitor which is preferred and has the above enumerated characteristics, the present invention also provides certain analogs of this inhibitor which exhibit characteristics, including leukocyte-elastase inhibitor activity, which are also desirable from a pharmaceutical standpoint. Accordingly, such analogs are also preferred compositions of the present invention. In particular, if the amino acid methionine were to be replaced by the amino acid valine, the resultant inhibitor would exhibit improved resistance to oxidative inactivation and, therefore, exhibit improved leukocyte elastase and cathepsin G inhibitor properties. Similar changes may be made to improve the inhibitor's resistance to inactivation by cigarette tar.

It is possible that additional substitutions will become apparent to those of ordinary skill in the art through the practice of the present invention which will enhance other various properties of the claimed protease inhibitor and will serve to make the resultant protein more useful as a proteolytic enzyme inhibitor. It is contemplated that such further substitutions are within the scope of the present invention.

Moreover, it is recognized by those skilled in the art that minor variations in the amino acid sequence of a protein, even if they do not enhance the function of the protein, create analogs which do not have significantly diminished activity. It is, therefore, contemplated that analogs of the protease inhibitors discussed above in which the sequences contain minor variations from that of the preferred sequence set forth above are included within the scope of the present invention. In particular, it is believed that minor alterations to the amino acid sequence at the C- and N-termini will not significantly alter the activity of the disclosed protease inhibitors. Specifically, substitution at the C- or N-terminus with a cyclized amino acid, for example proline, is believed to result in a protease inhibitor having the desired serine protease inhibiting activity. Also, analogs of the disclosed protease inhibitors which have alterations at the C- or N-terminus, which alterations do not destroy the serine protease inhibitor properties of the analog, are included within the scope of the present invention.

It is also contemplated that additions of polypeptide chains to the C- or N-terminus of the present protease inhibitors will be within the scope of the invention. In particular polypeptide chains may be joined to either terminus through protein fusion techniques. These additional polypeptides may serve to enhance the pharmacological efficacy of the instant protease inhibitors. For example, the polypeptide may, by fusion with other proteins, be made capable of anchoring in mucus membranes to cause the protease inhibitor to remain in a particular site, such as the lungs.

In these analogs, the variation to the amino acid sequence should not be such as to provoke an adverse immunological response in the organism to which the protease inhibitor is administered. The methods of determining whether a biological molecule will provoke adverse immunological response are known to those of ordinary skill in the art.

The foregoing substitutions may be effected by various methods. For example, the genetic instructions used to produce the inhibitor by recombinant DNA methods may be altered to cause a host microorganism to synthesize the desired analog. Such recombinant methods are set forth in the U.S. patent application Ser. No. 678,822 of Pradip K. Bandyopadhyay et al. entitled Recombinant Methods for Isolation of Serine Protease Inhibitors and DNA Sequences Useful for Same, filed Dec. 6, 1984 and U.S. patent application Ser. No. 803,471 of Pradip K. Bandyopadhyay et al. entitled "Recombinant Methods for Isolation of Serine Protease Inhibitors and DNA Sequences Useful for Same," filed Dec. 2, 1985, now abandoned. Other methods of biochemically synthesizing protein analogs are known to those of ordinary skill in the art and are intended to be included within the scope of the invention for creation of these and other analogs.

The protease inhibitor of the present invention and its analogs are contemplated for human and veterinary uses in the form of pharmaceutical products possessing serine protease inhibitor activity, particularly leukocyte elastase inhibitor activity. It is expected that pharmaceutical preparations containing, as at least one of the active ingredients, one of the present serine protease inhibitors would also contain appropriate, pharmaceutically acceptable carriers, diluents, fillers, binders and other excipients depending on the dosage form contemplated. For oral administration, steps must be taken to prevent degradation of the active protein in the digestive tract. Enteric coated dosage forms are contemplated as one form suitable for oral administration. If parenteral administration is chosen, the preparation may contain a water or saline solution or other pharmaceutically acceptable suspension agent. Generally, it would be preferred that a preparation intended for parenteral administration contain sodium chloride in sufficient concentrations to make the overall preparation isotonic to body fluids. It is also contemplated that pharmaceutical preparations containing the serine protease inhibitors, particularly leukocyte elastase inhibitor proteins, of the present invention can be administered locally, as by injection or topical application for treatment of localized enzyme imbalances. The present inhibitors, particularly leukocyte elastase inhibitor, may also be administered as an aerosol, particularly when applied to the lungs as in the treatment of emphysema. In these situations, suitable carriers, diluents and propellants would be used.

The amount of the protease inhibitor to be administered would be dependent in each dosage situation on the amount of excess proteolytic enzyme present in the organism. To determine the appropriate dosage, one would quantify the excessive amount of proteolytic enzyme present and would determine, based on the activity of the particular species of protease inhibitor or mixtures thereof to be administered, the total amount of protease inhibitor necessary to neutralize the excess proteolytic enzyme. Such a determination is routinely made by those of ordinary skill in the art in determining therapeutic dosages in treating immunological disorders and is within the ambit of tasks routinely performed by them without undue experimentation, especially in light of standard assays and the assays disclosed herein. However, it should be noted that it is believed that large excesses of the protease inhibitors of the present invention would not be toxic or cause an adverse reaction when administered to an organism with an excess of proteolytic enzymes. As such, it is preferred that an amount in excess of the optimal amount of protease inhibitor be administered, rather than a lesser amount than the optimum.

It is to be understood that application of the teachings of the present invention to a specific problem or environment will be within the capabilities of one having ordinary skill in the art in light of the teachings contained herein. Examples of the products of the present invention and representative processes for their isolation and manufacture appear in the following examples.

EXAMPLE 1

Purification of a Human Leukocyte Elastase Inhibitor from Parotid Secretions

Parotid secretions were collected from volunteers with a suction device fitted over the exit of the parotid ducts. Secretion was stimulated by sucking a sour candy. Two to three liters of pooled parotid secretions were brought to pH 6.0 with a sodium hydroxide solution and centrifuged to remove the precipitate. The supernatant was applied to a 2.5×40.0 cm column of SP Sephadex C50 equilibrated with 0.05M sodium acetate, pH 6.0, and 0.005M sodium chloride. The column was eluted with a linear gradient of 0.005 to 1M sodium chloride. The fractions obtained were tested for the presence of inhibitor by immunoassay. The fractions corresponding to the peak of activity were those that had been obtained near 0.6M. These fractions were concentrated to 3 ml by ultrafiltration through an Amicon UM2 filter and the concentrate was applied to a 1.6×100 cm column of Sephadex G50 equilibrated with 0.05M Tris HCl, pH 7.4, and 0.5M sodium chloride. The column was then eluted with this buffer and the fractions tested by immunoassay Active fractions were pooled and concentrated by ultrafiltration as described above. Between 2 and 4 mg of inhibitor were recovered which were essentially 100% active.

EXAMPLE 2

Purification of a Human Leukocyte Elastase Inhibitor from Purulent Bronchial Mucus Bronchial mucus was collected from hospital patients suffering from pulmonary diseases and pooled. The pools were frozen and lyophilized. The lyophilized powder was suspended in a cold solution of 5% perchloric acid and the mixture stirred vigorously for two hours and neutralised by the addition of 4M potassium hydroxide. The mixture was centrifuged at 12,000 g for 30 minutes at 0° C. to remove insoluble material.

The crude solution of proteins was fractionated by ultra-filtration through membranes designed to remove all material of molecular weight greater than 100,000 and smaller than 10,000 daltons. In the first step, the solution was recirculated over an Amicon XM100A membrane in a thin channel ultrafiltration apparatus. The material passing through the membrane was then passed through the same apparatus with the XM100A membrane replaced with a YM10 It was also possible to fractionate the material by initial recirculation over a Millipore 100K membrane in a Minitan apparatus. In this instance, the material passing through the filter was then passed through the same apparatus with a 10K membrane. In both cases, the material retained by the membranes was recovered for further processing.

The ultrafiltrates were chromatographed on a reverse phase high pressure liquid chromatography (hplc) column. Approximately one ml containing about 20 mg of protein total and about 0.6 mg of inhibitor was loaded on an RP8 column (obtained from Synchrom Inc., Linden, Ind.) at a flow rate of 1 ml per minute. The proteins were eluted with a 0.05% solution of trifluoroacetic acid in water and then with a linear gradient of 0 to 50% solution of 0.05% trifluoroacetic (TFA) acid in acetonitrile. Fractions were collected and assayed for protease inhibitor activity by mixing with a known amount of chymotrypsin and subsequently determining the residual active chymotrypsin using standard procedures described above. Active material was eluted between 25% and 30% acetonitrile solution. These fractions were pooled for further processing.

The pooled fractions from the RP8 column were lyophilized and dissolved in 0.05M sodium phosphate, pH 6.0, and applied to a Brownlee CX300 cation exchange column equilibrated with the same buffer. The column was eluted with a linear gradient of 0 to 100% 0.5M sodium phosphate, pH 60. Active fractions were again detected by their ability to inhibit chymotrypsin. Three peaks of activity were detected eluting at 0.24M, 0.26M, and 0.28M phosphate. Three pools of active material were made and these were desalted and concentrated in an Amicon apparatus with a YM10 membrane before being stored frozen.

The activity of each fraction was determined by assay against chymotrypsin and the protein concentration determined by Bradford assay (Analytical Biochem. 72:248 (1976)). Each peak had an activity against chymotrypsin which was about 80% of that observed for the inhibitor purified from the parotid secretions of Example 1.

EXAMPLE 3

The Determination of the Amino Acid Sequence of the Leukocyte Elastase Inhibitor Isolated from Parotid Secretions The native inhibitor was reduced and carboxymethylated by standard procedures. 1.0 mg (80 nmol) of the inhibitor was dissolved in 600 1 of a solution of 6M guanidinium hydrochloride in 0.1M Tris HCl, pH 8.0, containing 1.32 mol of dithiothreitol and Tris buffer, pH 8.0. After 1 hour at 37° C., 3.32 nmol of (2-$^3$H) iodoacetic acid was added and the incubation was continued at 37° C. for another hour. Then there was added 0.66 nmol of dithiothreitol and, after an hour incubation at 37° C., another 1.36 nmol of (2-$^3$H) iodoacetic acid. After 1 hour incubation at 37° C., the reaction mixture was dialysed extensively against Tris buffer, pH 8.0, containing 0.1M sodium chloride. The resulting solution was applied to a Synchrom RP8 hplc column and the products eluted from the column with 0.05% TFA in water and then with a linear gradient of 0.05% TFA in acetonitrile. The reduced carboxymethylated protein eluted at 22% acetonitrile solution as determined by the absorbance at 215 and 280 nm and by the ($^3$H) content of these fractions. This material was dried under vacuum for further use.

The reduced carboxymethylated protein was sequenced by automatic Edman degradation resulting in the identification of residues 1 to 41 of the amino acid sequence. These are as follows:
Ser-Gly-Lys-Ser-Phe-Lys-Ala-Gly-Val-Cys-Pro-Pro-Lys-Lys-Ser-Ala-Gln-Cys-Leu-Arg-Tyr-Lys-Lys-Pro-Glu-Cys-Gln-Ser-Asp-Trp-Gln-Cys-Pro-Gly-Lys-Lys-Arg-Cys-Cys-Pro-Asp-__-Cys-Gly-Ile-Lys-Cys-Leu-Asp-(Pro)-Val-Asp-.

The reduced carboxymethylated protein was subjected to digestion with mouse submaxillary protease and the resulting peptides separated by reverse phase hplc on a Synchrom RP8 column, using the same solutions and gradients as above. One of these peptides, eluting at 20% acetonitrile solution, was sequenced by automated Edman degradation and gave the following sequence:
Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly This same peptide was subjected to digestion with chymotrypsin giving two new peptides which were separated by reverse phase hplc on a Synchrom RP8 column, again as set forth above. One of these eluting at 17% MeCN acetonitrile was sequenced by automated Edman degradation and gave the following sequence:
Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-(Thr-Arg)

The reduced carboxymethylated protein was digested with Lys-C protease and the resulting peptides were separated by reverse phase hplc on a Synchrom RP8 column. A peak of ($^3$H) containing material eluting between 13% and 15% acetonitrile was subjected to Edman degradation which gave the following sequence.
Cys-Leu-Asp-Pro-Val-Thr-Asp-Pro-Asn-Pro-Thr-Arg-Arg-Lys-Pro-Gly-Lys.

The peptides obtained from the mouse submaxillary protease digestion of the reduced carboxymethylated inhibitor and eluting between 26% and 28% acetonitrile were sequenced by automated Edman degradation and gave the following sequence:
Arg-Lys-Pro-Gly-Lys-Cys-Pro-Val-Thr-Tyr-Gly-Gln-Cys-Leu-Met-Leu-Asn-Pro-Pro-Asn-Phe-Cys-Glu-Met-Asp-Gly-Gln-Cys-Lys-Arg-Asp-Leu-Lys-Cys-Cys-Met . . . .

The reduced carboxymethylated inhibitor was digested with V8 protease and the peptides separated by reverse phase hplc on a Synchrom RP8 column. The peptide eluting at 19% acetonitrile was sequenced by automated Edman degradation and gave the following sequence:
Met-Asp-Gly-Gln-Cys-Lys-Arg-Asp-Leu-Lys-Cys-Cys-Met-Gly-Met-Cys-Gly-Lys-Ser-Cys-Val-Ser-Pro-Val-Lys The peptide resulting from the submaxillary protease digestion of the reduced carboxymethylated inhibitor and eluting between 26% and 28% acetonitrile from a Synchrom RP8 column was digested further with trypsin. The resulting peptides were separated by reverse phase hplc on the same column and the peptide eluting at 9% acetonitrile was sequenced by manual Edman degradation to give the following sequence.
Ser-Cys-Val-Ser-Pro-Val-Lys-Ala A peptide of the same composition and sequence may be isolated from a Lys-C protease digest of the protein. This peptide elutes between 8 and 10% acetonitrile from a Synchrom RP8 column.

The reduced carboxymethylated protein was hydrolysed by heating in 6M hydrochloric acid and its constituent amino acids based on an approximate molecular weight of 14,000 from SDS-polyacrylamide gel electrophoresis, were determined to be:

Ala 3.5 Arg 5.8 Asp 8.5 Cys 15.7 Glu 5.2 Gly 10.6 His 0.0 Ile 1.0 Leu 5.0 Lys 16.2 Met 4.0 Phe 2.1 Pro 14.8 Ser 3.7 Thr 2.4 Tyr 2.1 Val 4.7

It was determined that the above data defined a set of overlapping peptides obtained from the reduced carboxymethylated inhibitor. The full sequence of the inhibitor is therefore as follows.

Ser-Gly-Lys-Ser-Phe-Lys-Ala-Gly-Val-Cys-Pro-Pro-Lys-Lys-Ser-Ala-Gln-Cys-Leu-Arg-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-Tyr-Gly-Gln-Cys-Leu-Met-Leu-Asn-Pro-Pro-Asn-Phe-Cys-Glu-Met-Asp-Gly-Gln-Cys-Lys-Arg-Asp-Leu-Lys-Cys-Cys-Met-Gly-Met-Cys-Gly-Lys-Ser-Cys-Val-Ser-Pro-Val-Lys-Ala

The predicted amino acid composition from a hydrochloric acid hydrolysate of this protein would be:

Ala 3 Arg 5 Asp 9 Cys 16 Gly 9 Glu 7 His 0 Ile 1 Leu 5 Lys 15 Met 4 Phe 2 Pro 13 Ser 6 Thr 4 Tyr 2 Trp 1 Val 5

Further, it is believed that all of the Cys residues are linked to each other to form disulfide bonds.

EXAMPLE 4

The Identity of the Elastase Inhibitor from Bronchial Mucus with That from Parotid Secretions The inhibitor eluting from the Brownlee CX300 column at 0.28M Phosphate was characterised as follows:

(a) A sample of the inhibitor was hydrolysed under standard conditions by heating in 6M Hydrochloric acid. The amino acid composition of the inhibitor is
Ala 3.8 Arg 5.0 Asp 8.8 Gly 11.3 Glu 6.3 His 0 Ile 1.3 Leu 5.0 Lys 13.8 Met 3.8 Phe 2.5 Pro 12.5 Ser 6.3 Thr 3.8 Tyr 1.3 Val 5.0

This is not significantly different from the amino acid composition of the inhibitor from the parotid or that calculated from the sequence described above.

(b) The inhibitor was reduced and carboxymethylated under the conditions described above for the inhibitor from the parotid. This protein was then digested with mouse submaxillary protease and the products analysed by reverse phase hplc on a Synchrom RP8 column. The digestion pattern looks indistinguishable from that of reduced carboxymethylated inhibitor from the parotid run at the same time except for the shape of the peak eluting between 31 and 35% acetonitrile, which peak varies in elution position even between different samples of the parotid inhibitor. This probably arises from chemical modifications of a single peptide.

(c) The inhibitor was subject to automated Edman degradation and gave the following amino acid sequence for the first 14 amino acids:
X-Gly-Lys-Y-Phe-Lys-Ala-Gly-Val-Z-Pro-Pro-Lys-Lys
where X, Y, and Z are amino acids recovered at a level too low to be identified.

The extensive similarity between the inhibitor isolated from bronchial mucus and that isolated from parotid secretions, together with the absence of any evidence for a difference between these two proteins indicates that they are identical or near identical.

EXAMPLE 5

Identification of Characteristics of the Inhibitor that Make it Suitable for Clinical Use as an Inhibitor of Leukocyte Elastase (a) A solution of the parotid inhibitor of Example 1 was added to a solution of leukocyte elastase in the presence of a pH 8.0 buffer and human serum albumin and the residual free enzyme was determined by assaying its ability to hydrolyze methoxysuccinyl-Ala-Ala-Pro-Val p-nitroanilide. The data fit a standard model of an enzyme-inhibitor interaction in which one inhibitor inactivated one enzyme and the dissociation constant of the enzyme-inhibitor complex is $5 \times 10^{-10}$M.

In analogous experiments the ability of the inhibitor to inhibit serveral other human proteases was determined. These dissociation constants are set forth in the table below.

| Serine Protease | Dissociation Constant of the Complex With Inhibitor of Example 1 at 25° C. and pH 7.8 |
|---|---|
| human leukocyte elastase | $5 \times 10^{-10}$M |
| human cathepsin G | $1.5 \times 10^{-8}$M |
| human trypsin | $1.5 \times 10^{-9}$M |
| human chymotrypsin | $1.5 \times 10^{-10}$M |
| human pancreatic elastase | $2 \times 10^{-8}$M |

(b) A solution of the parotid inhibitor in 0.2M Tris HCl, pH 7.8 was heated to 70° C. in a capped tube and samples were taken for assay at various times. The results indicated that the inhibitor lost activity with approximate first order kinetics and had a half-life of about 10 hours. This degree of stability is exceptional for a protein in solution and constitutes a significant advantage in the formulation of the protein for clinical use as an elastase inhibitor.

(c) A solution of the inhibitor in 70% formic acid was maintained at 37° C. for 40 hours and, when assayed was found to have retained at least 80% of its original activity.

(d) A solution of the inhibitor was treated with mouse submaxillary protease, clostripain, and thermolysin. Only the latter enzyme resulted in any significant loss of inhibitory activity over a 3 hour period at 37° C. This resistance to degradation by enzymes constitutes a significant advantage in the use of this protein as a leukocyte elastase inhibitor in vivo since it indicates the general resistance of the inhibitor to other enzymes of a type that might be present in purulent bronchial mucus.

(e) A solution of the inhibitor in 6M guanidinium hydrochloride and 30 mM dithiothreitol, presumed by analogy with other proteins to have lost all defined structure, recovered at least 90% of its native, inhibitory activity when oxidized glutathione was added in ten-fold excess of the dithiothreitol used, and the solution was diluted ten-fold with 25 mM Tris HCl, pH 9.0. This result indicates that the active structure of the protein is a stable structure of the polypeptide chain. The result further implies that the protein will remain active under a variety of harsh treatments and, even under some conditions which destroy activity, will retain the ability to recover activity when these conditions are reversed.

EXAMPLE 6

The location of the antielastase, antichymotrypsin, and antitrypsin sites of SLPI were located by site-directed mutagenesis of the gene for SLPI followed by expression of the inhibitor in *E. coli* and measurement of the $K_i$ of the variants for these enzymes. The results were as follows.

| Variant | $K_i$ Elastase | $K_i$ Chymotrypsin | $K_i$ Trypsin |
|---|---|---|---|
| Wild-type | 0.5 | 0.4 | 3 |
| Gly 72 | 6.5 | 1000 | 1000 |
| Phe 72 | 70 | 0.1 | 0.3 |
| Ala 72 | 400 | 13 | 0.3 |
| Val 72 | 0.4 | 27 | 110 |
| Lys 72 | 300 | 45 | 0.003 |
| Arg 72 | 2500 | 37 | 0.005 |
| Gly 73 | 0.4 | 65 | 950 |
| Lys 73 | 0.1 | 0.1 | 3 |
| Gly 74 | 0.5 | 3.5 | 6.9 |

It will be apparent to those skilled in the art that various modifications and variations can be made to the processes and products of the present invention. Thus it is intended that the present invention cover the modifications and variations of this invention provided they come within the scope of the appended claims and their equivalents.

What is claimed is:

1. A serine protease inhibitor protein comprising the amino acid sequence:

$R_1$-Gly-Lys-Ser-Phe-Lys-Ala-Gly-Val-Cys-Pro-Pro-Lys-Lys-Ser-Ala-Gln-Cys-Leu-$R_2$-Tyr-Lys-Lys-Pro-Glu-Cys-Gln-Ser-Asp-$R_{10}$-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-$R_{13}$-Gly-Gln-Cys-$R_8$-$R_3$-$R_9$-Asn-Pro-Pro-Asn-Phe-Cys-Glu-$R_4$-Asp-Gly-Gln-Cys-Lys-Arg-$R_{11}$-$R_{12}$-Lys-Cys-Cys-$R_5$-Gly-$R_6$-Cys-Gly-Lys-Ser-Cys-Val-Ser-Pro-Val-Lys-$R_7$, wherein $R_1$ is serine or proline;

$R_2$, $R_3$, $R_4$, $R_5$ and $R_6$ are independently selected from the group consisting of methionine, valine, alanine, phenylalanine, tyrosine, tryptophan, lysine, glycine and arginine;

$R_7$ is alanine or proline;

$R_8$ and $R_9$ are independently selected from the group consisting of methionine, valine, alanine, phenylalanine, tyrosine, tryptophan, lysine, glycine, leucine and arginine;

$R_{10}$ is selected from the group consisting of leucine, lysine, glutamic acid, glutamine and tryptophan;

$R_{11}$ is selected from the group consisting of leucine, lysine, glutamine and aspartic acid;

$R_{12}$ is selected from the group consisting of leucine, lysine, glutamic acid and glutamine; and $R_{13}$ is selected from the group consisting of tyrosine, glutamic acid and aspartic acid;

wherein, at least one of the amino acid residues $R_{10}$, $R_{11}$, $R_{12}$ and $R_{13}$ is a substituted residue as compared to parotid secretion-derived serine protease inhibitor in which $R_{10}$ is tryptophan, $R_{11}$ is aspartic acid, $R_{12}$ is leucine and $R_{13}$ is tyrosine.

2. A serine protease inhibitor according to claim 1, which inhibits the activity of at least one serine protease selected from the group consisting of trypsin, leukocyte elastase, cathepsin G, pancreatic elastase, plasma kallikrein and chymotrypsin.

3. A serine protease inhibitor according to claim 1, which inhibits the activity of at least two serine proteases.

4. A serine protease inhibitor according to claim 1, which inhibits the activity of trypsin and leukocyte elastase.

5. A serine protease inhibitor according to claim 1, wherein $R_8$ is arginine and the serine protease inhibitor inhibits the protease activity of plasma kallikrein.

6. A serine protease inhibitor according to claim 1, wherein $R_2$ is glycine and the serine protease inhibitor inhibits the protease activity of leukocyte elastase but not trypsin.

7. A serine protease inhibitor according to claim 1, wherein $R_3$, $R_8$ or $R_9$ is glycine and the serine protease inhibitor inhibits the protease activity of trypsin but not leukocyte elastase.

8. A serine protease inhibitor according to claim 1, further comprising a polypeptide fused to the C- or N-terminus of the serine protease inhibitor.

9. A pharmaceutical composition, comprising a serine protease inhibitor according to claim 1 and a pharmaceutically acceptable carrier.

10. A pharmaceutical composition according to claim 9, in a form suitable for delivery by a route selected from the group consisting of oral, parenteral, local, topical and aerosol administration.

11. A method of inhibiting serine protease activity in a patient, comprising administering an amount of a pharmaceutical composition according to claim 9.

12. A method of inhibiting serine protease activity according to claim 11, wherein said serine protease inhibitor is administered in the form of an aerosol.

13. A method of inhibiting serine protease activity according to claim 12 for the treatment of pulmonary disease involving protease/protease inhibitor imbalance.

14. A method of inhibiting serine protease activity according to claim 13 for the treatment of emphysema.

15. A pharmaceutical composition comprising a serine protease inhibitor protein according to claim 1 and a pharmaceutically acceptable excipient.

16. A pharmaceutical composition of claim 15 wherein said excipient is a pharmaceutically acceptable carrier, diluent, filler, binder, suspension agent, tonicity modifier or propellant.

17. A pharmaceutical composition of claim 15 formulated for aerosol application.

18. A pharmaceutical composition of claim 17 formulated for delivery to the lungs.

19. A pharmaceutical composition of claim 15 formulated for topical application.

20. A pharmaceutical composition comprising a serine protease inhibitor protein and a pharmaceutically acceptable excipient, wherein said protein comprises the amino acid sequence:

R1-Gly-Lys-Ser-Phe-Lys-Ala-Gly-Val-Cys-Pro-Pro-Lys-Lys-Ser-Ala-Gln-Cys-Leu-R2-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-Tyr-Gly-Gln-Cys-R8-R3-R9-Asn-Pro-Pro-Asn-Phe-Cys-Glu-R4-Asp-Gly-Gln-Cys-Lys-Arg-Asp-Leu-Lys-Cys-Cys-R5-Gly-R6-Cys-Gly-Lys-Ser-Cys-Val-Ser-Pro-Val-Lys-R7 or a portion of said protein having serine protease inhibitory activity, wherein R1 and R7 are amino acid residues;

R2, R3, R4, R5 and R6 are independently selected from the group consisting of methionine, valine, alanine, phenylalanine; tyrosine, tryptophan, lysine, glycine and arginine; and R8 and R9 are independently selected from the group consisting of methionine, valine, alanine, phenylalanine, tyrosine, tryptophan, lysine, glycine, leucine and arginine.

21. A pharmaceutical composition of claim 20 wherein said excipient is a pharmaceutically acceptable carrier, diluent, filler, binder, suspension agent, tonicity modifier or propellant.

22. A pharmaceutical composition of claim 20 formulated for aerosol application.

23. A pharmaceutical composition of claim 22 formulated for delivery to the lungs.

24. A pharmaceutical composition of claim 20 formulated for topical application.

25. A pharmaceutical composition comprising a serine protease inhibitor protein and a pharmaceutically acceptable excipient, wherein said protein comprises the amino acid sequence:
Ser-Gly-Lys-Ser-Phe-Lys-Ala-Gly-Val-Cys-Pro-Pro-Lys-Lys-Ser-Ala-Gln-Cys-Leu-Arg-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-Tyr-Gly-Gln-Cys-Leu-Met-Leu-Asn-Pro-Pro-Asn-Phe-Cys-Glu-Met-Asp-Gly-Gln-Cys-Lys-Arg-Asp-Leu-Lys-Cys-Cys-Met-Gly-Met-Cys-Gly-Lys-Ser-Cys-Val-Ser-Pro-Val-Lys-Ala.

26. A pharmaceutical composition of claim 25 wherein said excipient is a pharmaceutically acceptable carrier, diluent, filler, binder, suspension agent, tonicity modifier or propellant.

27. A pharmaceutical composition of claim 25 formulated for aerosol application.

28. A pharmaceutical composition of claim 27 formulated for delivery to the lungs.

29. A pharmaceutical composition of claim 25 formulated for topical application.

30. A method of treating a protease-mediated condition comprising administering a pharmaceutical composition of claim 20 or 25.

31. The method of claim 30 wherein said pharmaceutical composition is administered topically.

32. The method of claim 30 wherein said protease is a polymorphonuclear granulocyte protease.

33. The method of claim 30 wherein said protease is elastase or trypsin.

34. The method of claim 30 wherein said protease is chymotrypsin or cathepsin G.

35. A method of treating a pulmonary disease involving protease/protease inhibitor imbalance comprising administering a pharmaceutical composition of claim 20 or 25.

36. The method of claim 35 wherein said pharmaceutical composition is administered as an aerosol.

37. The method of claim 36 wherein said pharmaceutical composition is administered to the lungs.

* * * * *

UNITED STATES PATENT AND TRADEMARK OFFICE
CERTIFICATE OF CORRECTION

PATENT NO. : 5,900,400
DATED : May 4, 1999
INVENTORS : Thompson et al.

It is certified that error appears in the above-identified patent and that said Letters Patent is hereby corrected as shown below:

Title page, [56] U.S. 4,546,082, change "Kurgan" to --Kurjan--.

[56] Thompson et al., after "*USA*" add --83:--.

Column 11, line 36, change "pH 60" to --pH 6.0--.

Signed and Sealed this

Twelfth Day of October, 1999

Attest:

Q. TODD DICKINSON

Attesting Officer

Acting Commissioner of Patents and Trademarks